United States Patent
Lozano

(10) Patent No.: US 8,412,337 B2
(45) Date of Patent: Apr. 2, 2013

(54) SYSTEMS AND METHODS FOR TREATING PAIN USING BRAIN STIMULATION

(75) Inventor: Andres Lozano, Toronto (CA)

(73) Assignee: Functional Neuroscience, Inc., Toronto (CA)

( * ) Notice: Subject to any disclaimer, the term of this patent is extended or adjusted under 35 U.S.C. 154(b) by 0 days.

(21) Appl. No.: 13/366,330

(22) Filed: Feb. 5, 2012

(65) Prior Publication Data

US 2012/0289871 A1    Nov. 15, 2012

Related U.S. Application Data

(63) Continuation of application No. 13/071,122, filed on Mar. 24, 2011, now Pat. No. 8,116,877, which is a continuation of application No. 11/895,335, filed on Aug. 24, 2007, now Pat. No. 7,937,152.

(60) Provisional application No. 60/841,033, filed on Aug. 30, 2006.

(51) Int. Cl.
    *A61N 1/34* (2006.01)

(52) U.S. Cl. ........................................................ 607/46

(58) Field of Classification Search ...................... 607/46
    See application file for complete search history.

(56) References Cited

U.S. PATENT DOCUMENTS

| | | | |
|---|---|---|---|
| 3,731,681 A | 5/1973 | Blackshear | 128/214 |
| 3,951,147 A | 4/1976 | Tucker | 128/260 |
| 4,692,147 A | 9/1987 | Duggan | 604/93 |
| 4,772,263 A | 9/1988 | Dorman | 604/132 |
| 5,840,069 A | 11/1998 | Robinson | 604/131 |
| 6,036,459 A | 3/2000 | Robinson | 417/477.7 |
| 6,051,017 A | 4/2000 | Loeb | 607/1 |
| 6,109,269 A | 8/2000 | Rise | 128/898 |
| 6,176,242 B1 | 1/2001 | Rise | 128/898 |
| 6,356,784 B1 | 3/2002 | Lozano | 607/7 |
| 6,620,151 B2 | 9/2003 | Blischak | 604/892.1 |
| 6,666,845 B2 | 12/2003 | Hooper | 604/892.1 |
| 6,708,064 B2 | 3/2004 | Rezai | 607/45 |
| 6,735,474 B1 | 5/2004 | Loeb | 607/41 |
| 6,735,475 B1 | 5/2004 | Whitehurst | 607/46 |
| 6,920,359 B2 | 7/2005 | Meadows | 607/59 |
| 7,177,702 B2 | 2/2007 | Wallace | 607/116 |
| 2005/0010262 A1 | 1/2005 | Rezai | 607/46 |
| 2005/0143799 A1 | 6/2005 | Black | 606/129 |
| 2005/0203602 A1 | 9/2005 | Wallace | 607/116 |

OTHER PUBLICATIONS

U.S. Appl. No. 13/071,122, filed Mar. 24, 2011, Andres Lozano.
U.S. Appl. No. 11/895,335, filed Aug. 24, 2007, Andres Lozano.
U.S. Appl. No. 60/841,033, filed Aug. 30, 2006, Andres Lozano.
U.S. Appl. No. 11/978,285, filed Oct. 29, 2007, Andres Lozano.
Issue Notification mailed Apr. 13, 2011 for U.S. Appl. No. 11/895,335, filed Aug. 24, 2007 (Inventor: Andres Lozano) (1 page).
Response to 312 Amendment mailed Mar. 28, 2011 for U.S. Appl. No. 11/895,335, filed Aug. 24, 2007 (Inventor: Andres Lozano) (5 pages).
Amendment under Rule 312 filed Mar. 19, 2011 for U.S. Appl. No. 11/895,335, filed Aug. 24, 2007 (Inventor: Andres Lozano) (5 pages).
Notice of Allowance mailed Dec. 28, 2010 for U.S. Appl. No. 11/895,335, filed Aug. 24, 2007 (Inventor: Andres Lozano) (8 pages).
Response to Final Office Action filed Nov. 22, 2010 for U.S. Appl. No. 11/895,335, filed Aug. 24, 2007 (Inventor: Andres Lozano) (9 pages).
Notice of Abandonment mailed Nov. 24, 2010 for U.S. Appl. No. 11/895,335, filed Aug. 24, 2007 (Inventor: Andres Lozano) (2 pages).

(Continued)

*Primary Examiner* — Carl H Layno
*Assistant Examiner* — Jeremiah Kimball
(74) *Attorney, Agent, or Firm* — Ballard Spahr LLP

(57) ABSTRACT

The invention comprises systems and methods for treating nociceptive pain including at least one force-regulatable device in mechanical, electrical, or chemical communication with at least one brain area identified as processing nociceptive pain signals. The force-regulatable device acts to alter the nociceptive pain signals in a brain area to alleviate nociceptive pain.

15 Claims, 3 Drawing Sheets

OTHER PUBLICATIONS

Notice of Appeal filed for Jul. 22, 2010 for U.S. Appl. No. 11/895,335, filed Aug. 24, 2007 (Inventor: Andres Lozano) (2 pages).
Final Rejection mailed Jan. 26, 2010 for U.S. Appl. No. 11/895,335, filed Aug. 24, 2007 (Inventor: Andres Lozano) (11 pages).
Response after Non-Final filed Oct. 29, 2009 for U.S. Appl. No. 11/895,335, filed Aug. 24, 2007 (Inventor: Andres Lozano) (16 pages).
Non-Final Rejection mailed May 29, 2009 for U.S. Appl. No. 11/895,335, filed Aug. 24, 2007 (Inventor: Andres Lozano) (12 pages).
Hsieh et al. (1995) Traumatic nociceptive pain activates the hypothalamus and the periaqueductal gray: a positron emission tomography study. Pain. 64: 303-314.
Lenzlinger et al. (2001) The duality of the inflammatory response to traumatic brain injury. Mol Neurobiol. 24(1-3): 169-181.
Notice of Abandonment mailed Feb. 3, 2010 for U.S. Appl. No. 11/978,285, filed Oct. 29, 2007 (Inventor: Andres Lozano) (2 pages).
Non-Final Rejection mailed Jul. 8, 2009 for U.S. Appl. No. 11/978,285, filed Oct. 29, 2007 (Inventor: Andres Lozano) (4 pages).
Response to Restriction Requirement filed May 8, 2009 for U.S. Appl. No. 11/978,285, filed Oct. 29, 2007 (Inventor: Andres Lozano) (6 pages).
Restriction Requirement mailed Mar. 11, 2009 for U.S. Appl. No. 11/978,285, filed Oct. 29, 2007 (Inventor: Andres Lozano) (8 pages).
Issue Notification mailed Jan. 25, 2012 for U.S. Appl. No. 13/071,122, filed Mar. 24, 2011 (Inventor: Andres Lozano) (1 page).
Communication mailed Oct. 27, 2011 for U.S. Appl. No. 13/071,122, filed Mar. 24, 2011 (Inventor: Andres Lozano) (2 pages).
Notice of Allowance mailed Oct. 11, 2011 for U.S. Appl. No. 13/071,122, filed Mar. 24, 2011 (Inventor: Andres Lozano) (8 pages).
Second Preliminary Amendment filed Sep. 19, 2011 for U.S. Appl. No. 13/071,122, filed Mar. 24, 2011 (Inventor: Andres Lozano) (5 pages).
First Preliminary Amendment filed Mar. 24, 2011 for U.S. Appl. No. 13/071,122, filed Mar. 24, 2011 (Inventor: Andres Lozano) (3 pages).

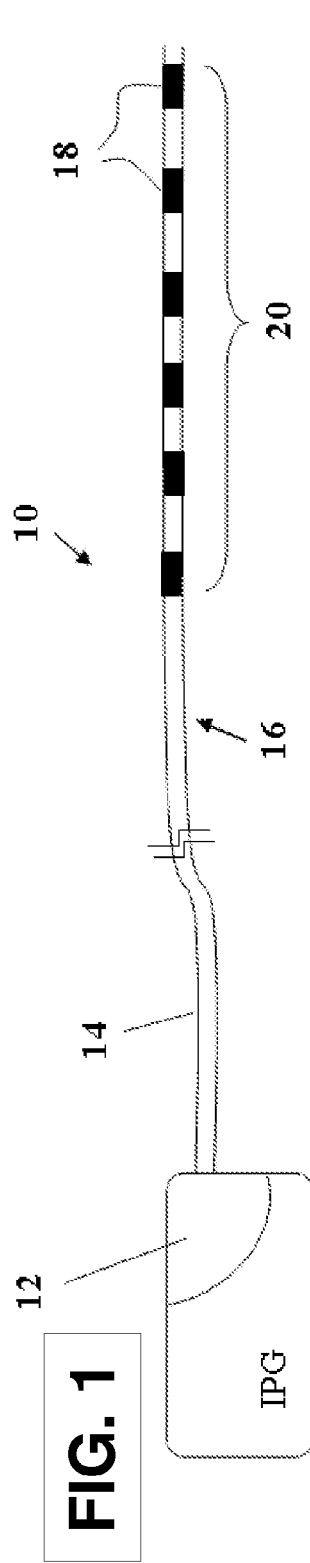
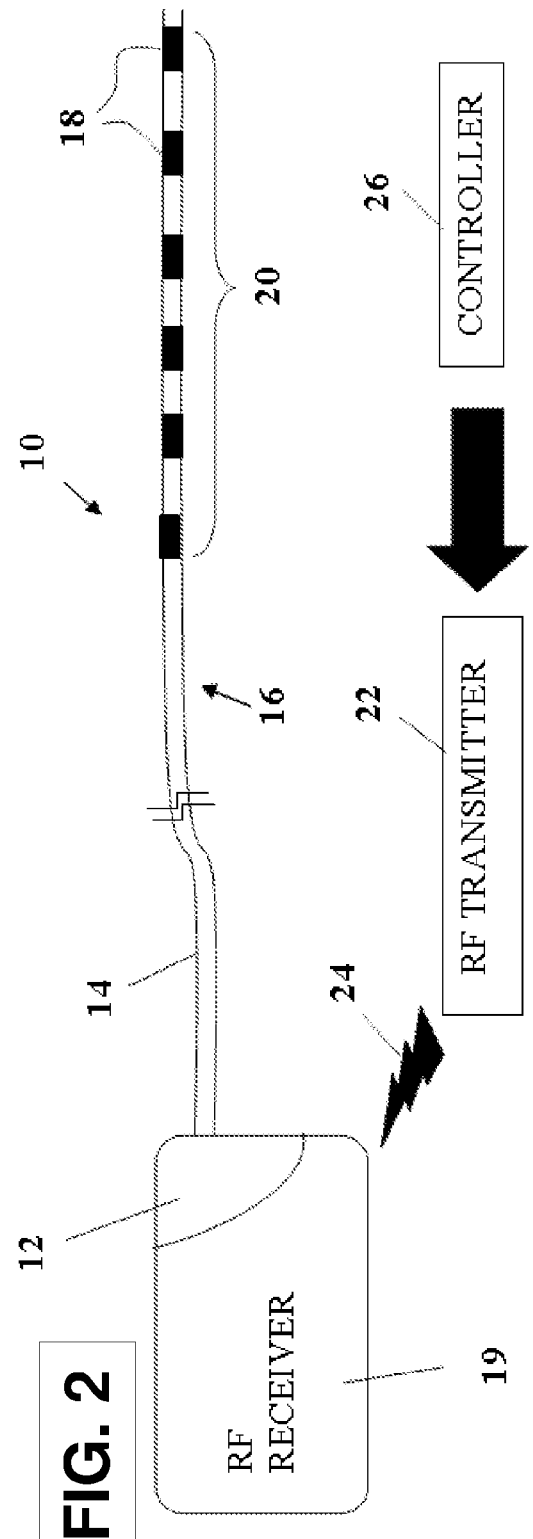

SYSTEMS AND METHODS FOR TREATING PAIN USING BRAIN STIMULATION

RELATED APPLICATIONS

The present application is a continuation of U.S. patent application Ser. No. 13/071,122 filed Mar. 24, 2011 (now U.S. Pat. No. 8,116,877), which is a continuation of U.S. patent application Ser. No. 11/895,335, filed Aug. 24, 2007 (now U.S. Pat. No. 7,937,152), which claims priority to U.S. Provisional Patent Application No. 60/841,033, filed Aug. 30, 2006, which applications are incorporated herein in their entirety.

TECHNICAL FIELD

The invention relates to systems and methods for treating pain by mechanical, electrical, or chemical stimulation of the brain. More particularly, the invention is directed to a method for modulating chronic nociceptive pain via stimulation of one or more areas of the brain, such as the motor cortex of the brain.

BACKGROUND

Pain is broadly defined as an unpleasant sensory experience associated with actual or potential tissue damage, or described in terms of such damage. The interpretation of sensory pain occurs when peripheral nerve endings called nociceptors are stimulated and subsequently transmit signals through sensory neurons in the spinal cord. The signals are then transmitted to the brain, at which point the individual becomes aware of the pain.

There are a number of pain categories and classifications. For example, the experience of physiological pain can be grouped into four categories according to the source and related nociceptors.

First, cutaneous pain is caused by injury to the skin or superficial tissues. Cutaneous nociceptors terminate just below the skin, and due to the high concentration of nerve endings, produce a well-defined, localized pain of short duration. Example injuries that produce cutaneous pain include paper cuts, minor burns (e.g., first degree burns) and superficial lacerations.

Second, somatic pain originates from ligaments, tendons, bones, blood vessels, and even nerves themselves, and is detected with somatic nociceptors. The scarcity of nociceptors in these areas produces a sharp, aching, pain of longer duration than cutaneous pain and somewhat less localized. Examples include a sprained ankle or broken bones.

Third, visceral pain originates from body organs. Visceral nociceptors are located within body organs and internal cavities. Similar to somatic pain, a scarcity of nociceptors in these areas produces a pain usually more aching and of a longer duration than somatic pain. Visceral pain may be more difficult to localize. Injuries to visceral tissue may exhibit "referred" pain, where the sensation is localized to an area completely unrelated to the site of injury. Myocardial ischaemia (i.e., the loss of blood flow to a part of the heart muscle tissue) is an example of referred pain; the sensation can occur in the upper chest as a restricted feeling, or as an ache in the left shoulder, arm, or hand. Another example of referred pain is phantom limb pain. Phantom limb pain is the sensation of pain from a limb that a person no longer has or from which the person no longer receives physical signals. This phenomena—also known as deafferentation pain—is almost universally reported by amputees and quadriplegics.

Fourth, neuropathic pain (e.g., "neuralgia") can occur as a result of injury or disease to the nerve tissue itself. The injury or disease can disrupt the ability of the sensory nerves to transmit correct information to the thalamus or cortex. Consequently, the brain interprets painful stimuli even though there is no obvious or documented physiologic cause for the pain.

Other pain classifications include acute pain and chronic pain. Acute pain is defined as short-term pain or pain with an easily identifiable cause. Acute pain indicates present damage to tissue or disease and may be "fast" and "sharp" followed by aching pain. Acute pain is centralized in one area before becoming somewhat spread out. Acute pain generally responds well to medications (e.g., morphine).

Chronic pain may be medically defined as pain that has lasted six months or longer. This constant or intermittent pain has often outlived its purpose because it does not help the body to prevent injury. It is often more difficult to treat than acute pain. Expert care is generally necessary to treat any pain that has become chronic. In addition, stronger medications are typically used for extended periods in an attempt to control the pain. This can lead to drug dependency. For example, opioids are used in some instances for prolonged periods to control chronic pain. Drug tolerance, chemical dependency, and even psychological addiction may occur.

Debilitating chronic pain affects tens of millions of people annually. Accordingly, this costs hundreds of millions of dollars in terms of medication, physical therapy, and lost production. The current methods for treating chronic pain have a limited success rate and in some cases may result in chemical dependency.

What is needed are safe, effective systems and methods for treating chronic, debilitating, nociceptive pain that deliver appropriate mechanical, electrical, or chemical stimulation directly to specific brain regions. In addition, effective methods are needed that may reduce the need for habit-forming pain-relieving drugs or minimize the need for such drugs by maximizing their effectiveness through direct application in specific brain regions.

SUMMARY

The present invention comprises systems and methods for the treatment of nociceptive pain using mechanical, electrical, or chemical stimulation applied to one or more areas of the brain. The mechanical, electrical, or chemical stimulus alters the nociceptive pain signals in the brain area to alleviate pain, such as chronic pain. In certain embodiments, the method of the invention comprises mechanical stimulation to treat pain. In other embodiments, the method of the invention comprises electrical stimulation or chemical stimulation (e.g., one or more chemicals) to treat pain. In yet other embodiments of the invention, methods comprise a combination of mechanical, electrical, or chemical stimulation to treat pain.

According to an embodiment of the invention, the stimulation may induce a change in the electrical activity of the underlying brain structures to inhibit nociceptive pain, deafferent pain, or a movement disorder (e.g., tremor). Such stimulation is likely to be produced by mechanical stimulation, electrical stimulation or chemical stimulation. Examples of chemical stimulation include, but are not limited to, ionic solutions, containing, for example, potassium ions ($K^+$) or sodium ions ($Na^+$), neurotransmitters (e.g., norepinephrine, glycine, aspartic acid (i.e., aspartate), glutamic acid (i.e., glutamate), gamma-amino butyric acid (GABA), acetylcholine, dopamine, or serotonin, medications that increase the level of a neurotransmitter (e.g., flouxetine, Prozac®), trazodone), chemicals or compounds that act to inhibit axonal or neuronal activity (e.g., local anaesthetics such as lidocaine or marcaine), or a drug that acts to block pain (e.g., a pain reliever such as morphine or its derivatives or opioid peptides such as endorphins, enkephalins, or dynorphins). Other chemicals or compounds are known to those of ordinary skill in the art.

In one embodiment of the methods of the present invention, a brain area that processes nociceptive pain signals is contacted using a force-regulatable device. The methods further include applying mechanical, electrical, or chemical stimulation to the brain area and alleviating nociceptive pain by altering the nociceptive pain signals in the brain area. The method may further comprise techniques for identifying the brain area, such as visualizing the cortex using magnetic resonance imaging, functional magnetic resonance imaging, or positron emission tomography. More specific areas of the brain, such as the motor cortex, the primary motor cortex, the premotor cortex, or the supplementary motor cortex may also be visualized by evoked potentials or direct cortical stimulation.

Another embodiment of the methods of the present invention comprises applying mechanical stimulation manually or automatically by surgically implanting a force-regulatable device. One example of a force-regulatable device is a collapsible/expandable electrode.

Yet another embodiment of the methods of the present invention comprises applying electrical stimulation by supplying at least one force-regulatable device with electrical power. The force-regulatable device may be in communication with an electrical power source to provide electrical stimulation to the brain area, such as the motor cortex area. Furthermore, the force-regulatable device may be fixed about the brain area (e.g., epidurally or subdurally).

The force-regulatable device may be in communication with an electrical power source, a mechanical power source, or a chemical source. The brain area may be, for example, the cortex, including the primary and secondary sensory cortex, the motor cortex, the primary motor cortex, the premotor cortex, or the supplementary motor cortex. The force-regulatable device may further be in communication with the brain area via implanting an epidural or subdural force-regulatable device (such as a collapsible/expandable electrode) to the dura such that the force-regulatable device exerts a mechanical force on the brain area (e.g., the primary motor cortex) when the surgical procedure is finished.

In yet another aspect, the invention comprises a system for using functional imaging to identify and target areas of abnormal brain activity relative to chronic nociceptive pain. In this manner, altering the nociceptive pain signals in the identified brain area are customized or individualized for a given patient. In one embodiment, the system for using functional imaging to identify and target areas of abnormal brain activity compares baseline brain activity in pain patients with that of control subjects without pain. In another example, the pain patients are given a pain stimulus—such as heat applied to the skin—to more precisely map the brain area activated by the painful stimulus and thus target this area for disruption or alteration of nociceptive pain signals, thus alleviating chronic nociceptive pain. Brain areas in which this could be accomplished include, but are not limited to, the cingulate lobe, the insula, the sensory cortex, and the motor cortex (i.e., the motor cortex, the premotor cortex, the primary motor cortex, or the supplementary motor cortex areas). The imaging could be accomplished using, for example, functional magnetic resonance imaging, magnetoencephalography, evoked potentials, magnetoencephalography after magnetic resonance imaging, or positron emission tomography. Other imaging techniques are known to those of ordinary skill in the art. In another embodiment, the system for using functional imaging to identify and target areas of abnormal brain activity may utilize imaging machines designed for intraoperative imaging such that pain patients may act as his or her own control to identify and target areas of abnormal brain activity relative to chronic nociceptive pain.

The foregoing has outlined rather broadly the features and technical advantages of the present invention. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

FIG. 1 illustrates an exemplary electrical stimulation system comprising an internal pulse generator.

FIG. 2 illustrates an exemplary electrical stimulation system comprising a radio frequency transmitter and receiver.

DETAILED DESCRIPTION

Figure 3:
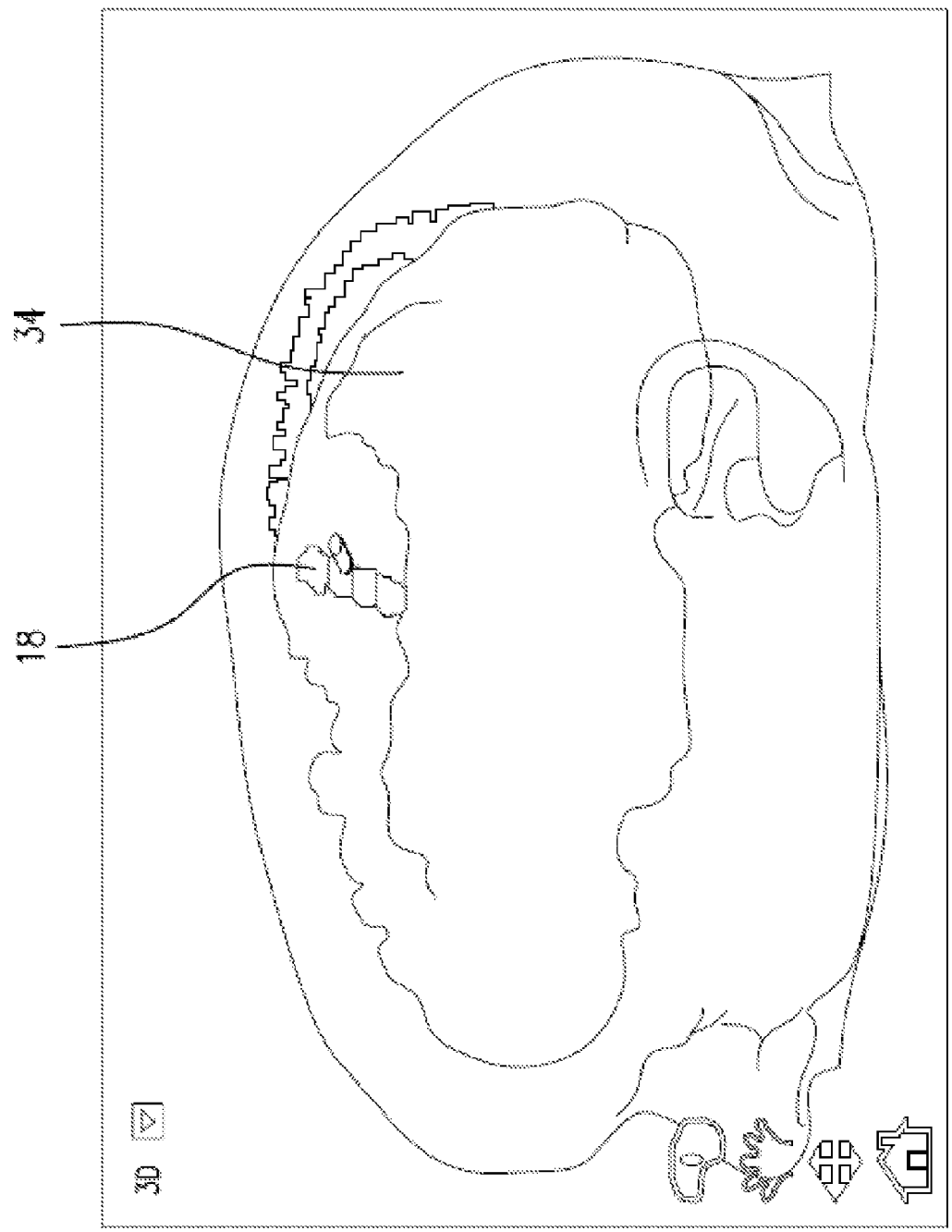
FIG. 3 illustrates a three-dimensional illustration of the left hemisphere of a human brain showing the placement of electrodes along the motor cortex.

The present invention relates to systems and methods for treating or alleviating nociceptive pain, such as chronic nociceptive pain. The methods of the invention are suited for relieving debilitating chronic nociceptive pain associated with, various medical conditions, including, for example, arthritis. The method of the invention comprises providing a force-regulatable device (e.g., at least one electrode) such that the force-regulatable device is in physical, electrical, or chemical communication with the brain.

A stimulus is provided to at least one brain area to affect the perception, nature, severity, character and associated suffering of nociceptive pain by a subject or patient. A stimulus may comprise electrical stimulation, provision of chemical agents, compounds or pharmaceuticals, or mechanical modulation, or combination of two or more of these. As used herein, stimulus and mechanical, electrical, or chemical stimulation are used interchangeably.

As used herein, the term "in communication" may refer to physical contact, one or more electrical stimulation leads, or catheters being adjacent, in the general vicinity, in close proximity, or directly next to, or in direct contact or directly inserted in the predetermined stimulation site. Thus, one of skill in the art understands that the one or more electrical stimulation leads or catheters are "in communication" with the predetermined site of the brain if the stimulation results in a modulation of neuronal activity associated with the site. In addition, "in communication" with brain tissue encompasses surrounding or adjacent white matter tracts or fibers leading to and from the brain tissue and/or white matter tracts or fibers that are contiguous with the brain tissue.

One embodiment of the present invention comprises methods for treating pain comprising contacting a brain area that processes nociceptive pain signals with a force-regulatable device, applying mechanical, electrical, or chemical stimulation to the brain area, and alleviating nociceptive pain by altering the nociceptive pain signals in the brain area. The method may further comprise identifying the brain area that processes nociceptive pain prior to contacting the brain area with the force-regulatable device.

Identifying a brain area involved in processing nociceptive pain signals may be accomplished, for example, using magnetic resonance imaging (MRI), functional magnetic resonance imaging (fMRI), positron emission tomography (PET), functional positron emission tomography, electroencephalogram (EEG), evoked potentials (i.e., by phase reversal at the central sulcus), or direct cortical stimulation in an awake and non-paralyzed patient. In addition, different areas of the brain may be selected, such as the motor cortex including but not limited to the primary motor cortex area, the premotor cortex area, or the supplementary motor cortex area. Other areas of the brain in which the methods of the present invention are applied include, but are not limited to, the nucleus accumbens, thought to be associated with reward processing; the anterior limb of the internal capsule, which is thought to be involved in reward and judgment processing; the cingulated gyrus, including Brodmann area 25, and the subcallosal area involved in pain, suffering and depression; the insula, thought to be involved in pain processing; orbital frontal and medial frontal lobes; and the dorsolateral frontal lobe.

Briefly, MRI is a noninvasive diagnostic technique that produces computerized images of internal body tissues and is based on nuclear magnetic resonance of atoms within the body induced by the application of radio waves. Functional MRI is distinguished by using the magnetic resonance images to demonstrate correlations between physical changes (as in blood flow) in the brain and mental functioning (as in performing cognitive tasks).

PET is a diagnostic examination that involves the acquisition of physiologic images based on the detection of radiation from the emission of positrons. Positrons are tiny particles emitted from a radioactive substance administered to the patient. The subsequent images of the human body developed with this technique are used to evaluate a variety of diseases.

An electroencephalograph (EEG) is an apparatus for detecting and recording brain waves. The brain waves are recorded as traces using an electroencephalogram.

Another embodiment of the present invention includes systems and methods for surgically implanting a device or stimulation system in communication with a brain area, for example, the motor cortex area of a brain. The device or stimulation system is operated to apply a force (e.g., a mechanical, chemical, or electrical force), stimulating the brain area and alleviating nociceptive pain. The device or stimulation system may be a force-regulatable device. A force-regulatable device is defined herein as a device capable of administering regulated amounts of one or more of mechanical force, electrical stimulation, or chemical stimulation as further defined herein. For example, a force-regulatable device may include a collapsible/expandable electrode or a bulb-type device capable of changing shape in order to apply mechanical pressure to a brain area. By way of further example, a force-regulatable device may include an electrode capable of applying various amounts of electrical power to a brain area. By way of further example, a force-regulatable device may include a device capable of administering at least one chemical compound or solution to a brain area.

The force-regulatable device may include, for example, a probe, an electrode, or an electrode assembly (i.e., electrical stimulation lead), a chemical delivery assembly, such as a catheter, or combinations of these (e.g., a catheter having at least one electrical stimulation lead), or a signal generator or signal source (i.e., an electrical signal source, a chemical signal source, such as a chemical delivery pump, or magnetic signal source). The electrode may be coupled to an electrical signal source, an electrical power supply, a chemical delivery pump, or any combination thereof. The probe is operated to stimulate the predetermined treatment site. Furthermore, the probe and the signal generator or source can be incorporated together, wherein the signal generator and force-regulatable device are formed into a unitary or single unit. Such a unit may include one or more electrodes. These devices may be known as microstimulators. An example of a device suitable for the present invention is, for example, Bion®, which is manufactured by Advanced Bionics Corporation.

Applying a mechanical force may include surgically implanting a force-regulatable device, such as a collapsible/expandable electrode similar to that found in U.S. Patent Application Publication No. 20050203602 to Wallace et al., herein incorporated by reference in its entirety. The collapsible/expandable electrode may be adapted for surgical implantation. In this manner, the collapsible/expandable electrode may physically administer the beneficial effects of mechanical stimulation and, if necessary, to administer the beneficial effects of electrical stimulation, chemical stimulation, or any combination thereof. The collapsible/expandable aspect of the electrode may be permanent or continuous, transient, or intermittent. The collapsible/expandable aspect of the electrode may further be adjustable (i.e., a force-regulatable device) to suit the needs of the patient. In addition, the collapsible/expandable aspect of the electrode may be manually adjusted by the patient or incorporated into or associated with a detectable signal, such as the sensation of pain, to automatically apply or withdraw a mechanical force upon the sensation or cessation of pain, as appropriate. The electrode may be subdurally or epidurally secured about a brain area (e.g., the motor cortex area) and in communication with a pulse generator to provide electrical stimulation to the motor cortex.

In addition, the initial mechanical force applied by the force-regulatable device may occur by virtue of surgically implanting the force-regulatable device in or about the targeted brain area.

In a similar fashion, a force-regulatable device may deliver electrical or chemical stimulation to the brain site. The mechanical, electrical and/or chemical stimulation may be continuous, transient or infrequent, or may be intermittent, such as in a regular or irregular pattern of administration. The stimulation may be initiated by the patient in response to the perception of pain, or may be initiated and/or maintained using a programmed controller to provide stimulation in a continuous, infrequent or intermittent manner. Such control of stimulation initiation or maintenance may be accomplished by a microprocessor, by manual or mechanical means, or other programmable methods known to those skilled in the art.

It is envisioned, for example, that the predetermined site is a cortex area, such as a motor cortex area. A motor cortex area includes, but is not limited to, the primary motor cortex, the premotor cortex, and the supplementary motor cortex area. Modulating the motor cortex area via electrical stimulation, chemical stimulation (e.g., using a pharmaceutical), or mechanical stimulation can result in increasing, decreasing, masking, altering, overriding, or restoring neuronal activity resulting in alleviation of chronic nociceptive pain. Yet further, stimulation of a motor cortex area may result in modulation of neuronal activity of other areas of the brain, for example, the striatum (i.e., the caudate and putamen), globus pallidus, and the thalamus.

In another aspect, the present invention comprises a method for treating chronic nociceptive pain by implanting at least one force-regulatable device in mechanical, electrical, or chemical communication with a brain area that processes nociceptive pain signals and applying mechanical, electrical, or chemical stimulation to the brain area. The force-regulatable device may further be in communication with an electrical power source, a mechanical power source, or a chemical source. As described herein, the method of the invention comprising the implantation of the force-regulatable device may include identifying the brain area that processes nociceptive pain signals prior to the implantation.

In one embodiment, the method of the present invention comprises implanting a collapsible/expandable force-regulatable device about the dura (e.g., epidurally or subdurally) such that the collapsible/expandable force-regulatable device exerts a mechanical force on the brain area. Accordingly, the mechanical force acts to disrupt or alter the nociceptive pain signals in the brain area and alleviate the nociceptive pain. The collapsible/expandable force-regulatable device may include various settings in order to be manually or automatically adjusted to provide an appropriate level of pain relief to the patient. Automatic adjustments, for example, may be determined by the force-regulatable device based on a detectable signal, such as the amount of nociceptive pain perceived by the patient. The force-regulatable device may further communicate with the brain area identified as processing nociceptive pain signals by applying electrical stimulation at from about 1 V to about 25 V and from about 10 Hz to about 200 Hz frequency; or alternatively at from about 1 V to about 5 V and from about 110 Hz to about 135 Hz frequency.

A force-regulatable device may further be adapted to apply a neurotransmitter, a pain reliever, or other chemical to the brain area. For example, the force-regulatable device may be adapted with a catheter, a pump, and a discharge portion for infusing a dosage of a chemical, wherein after implantation the discharge portion of the catheter is in communication with the brain area identified as processing nociceptive pain signals. Operating the pump to discharge the chemical through the discharge portion of the catheter into the identified brain area thereby treats the chronic nociceptive pain.

It is envisioned that chemical stimulation can be performed independently of or in combination with electrical or mechanical stimulation. Examples of chemical stimulation include, but are not limited to, ionic solutions containing, for example, potassium ($K^+$) or sodium ($Na^+$), neurotransmitters (e.g., norepinephrine, glycine, aspartic acid (i.e., aspartate), glutamic acid (i.e., glutamate), gamma-amino butyric acid (GABA), acetylcholine, dopamine, or serotonin), medication that increases the level of a neurotransmitter (e.g., flouxetine (i.e., Prozac®), trazodone), or a drug that acts to block pain (e.g., a pain reliever such as morphine or its derivatives or opioid peptides such as endorphins, enkephalins, or dynorphins).

In another aspect, the present invention comprises systems for treating chronic nociceptive pain that include a force-regulatable device in mechanical, electrical, or chemical communication with a brain area that processes nociceptive pain signals, wherein the force-regulatable device is implanted about a patient's body to alter the nociceptive pain signals in the brain area. The system of the present invention may further include identifying the brain area involved in processing nociceptive pain signals prior to implanting the force-regulatable device. In addition to the techniques described herein used to identify a brain area, the system of the invention may also include identifying a brain area that processes nociceptive pain signals using a painful heat stimulus.

Mechanical force applied to the brain area upon implanting the force-regulatable device serves to disrupt or alter the nociceptive pain signals in the identified brain area. In addition, the force-regulatable device implanted about the identified brain area may be collapsible and/or expandable to enhance the mechanical communication of the force-regulatable device with the identified brain area. The mechanical force may be controlled manually or automatically by, for example, a fluid-controlled or fluid-operated pump.

The force-regulatable device may further be in electrical communication with at least an electrical power source (e.g., a pulse generator) in order to apply electrical stimulation to the brain area and provide another means to disrupt or alter the nociceptive pain signals in the identified brain area, alleviating chronic nociceptive pain. The pulse generator may be manual (i.e., the patient turns the pulse generator on or off depending on the pain level) or programmable (e.g., a closed loop system that turns itself on or off when it recognizes certain parameters, such as sensation or cessation of pain, respectively). Furthermore, the signal or pulse generator may be implanted in the patient's body.

The methods of the present invention, whether comprising electrical stimulation, chemical or mechanical modulation may be provided to the brain area of the patient in an on-going continuous manner, or may be controlled or regulated by the patient or by a care-giver. A device for providing the electrical stimulation, chemical or mechanical modulation may be in a closed loop system wherein the delivery of the stimulus, which may be electrical stimulation, chemical or mechanical modulation, is controlled. Control of the delivery of the stimulus and the determination of initiation, continuation, adjustment of amount, level, rate, location, or cessation of the stimulus may be provided in response to a predetermined signal. Such a predetermined signal may be a physiological change in the patient, including but not limited to, an electrical signal from for example, an EEG, field potential, evoked potential, or a neuronal firing pattern; a chemical signal, for example, a change in concentration of lactate, potassium ions, or pH in bodily fluid or structure; or a physical signal such as tissue pressure, temperature, change in optical properties of the tissue, change in motor function such as cessation of tremor, or a change resulting from lowered pain perception or autonomic response to pain (including breathing rate, heart rate, blood pressure and galvanic skin response). Such a predetermined signal may be a particular reading or setting from a monitoring device that measures one or more physiological parameters of the patient. The predetermined signals are detected, processed and used to control the delivery of the stimulus. Signal detection and the resulting signal processing steps may be located locally or remotely from the site of therapeutic delivery of the stimulus.

Mechanical and chemical communication may further include a localized regulatable inflammatory response in or about the identified brain area to disrupt or alter the nociceptive pain signals. In this manner, mechanical communication may be accomplished by implanting the force-regulatable device as described. The surgical implantation of the force-regulatable device applies pressure to the brain tissue, inducing a localized inflammation. Therefore, using a collapsible/expandable electrode may enable this benefit to remain (under manual control by the patient or under automatic control of the force-regulatable device) after the initial mechanical benefits of surgical implantation have waned. Chemical communication may be accomplished by administering a controlled amount of inflammatory agent to induce a localized regulatable inflammatory response in or about the identified brain area to disrupt or alter the nociceptive pain signals.

An example of a system for treating chronic nociceptive pain is a catheter having a proximal end coupled to a pump and a discharge portion for infusing a dosage of a chemical, wherein after implantation the discharge portion of the catheter is in communication with a predetermined stimulation site in the brain; and a pump to discharge the pharmaceutical through the discharge portion of the catheter into the predetermined stimulation site. A system may further comprise a control means for controlling the pump, so as to deliver the stimulation agent (such as a chemical compound, pharmaceutical, ionic solution, etc., or electrical or mechanical force) one time or multiple times.

Still further, another system comprises a device that is surgically implanted into the subject such that the device is in communication with a predetermined site, for example the motor cortex area. One such device is a microstimulator (i.e., Bion®, manufactured by Advanced Bionics Corporation) in which the device contains a generating portion and at least one electrode in a single unit. In further embodiments, a lead assembly is associated with at least one electrode and communicates with a power source (e.g., the Restore®, . Synergy®, or Itrel® systems manufactured by Medtronic, Inc.) such that the lead can stimulate the predetermined site not in direct contact with the power source.

Electrical Stimulation Devices

FIGS. 1 and 2 illustrate example force-regulatable systems or devices 10 used to provide brain stimulation. The force-regulatable stimulation device 10 generates and applies a stimulus to a target area of the brain, such as a motor cortex area, or alternatively the primary motor cortex area. The target area may also include the premotor cortex area or the supplementary motor area.

In general terms, FIG. 1 shows the force-regulatable stimulation device 10 that includes an implantable electrical stimulation source 12 (e.g., a power source or an internal pulse generator) and an implantable electrical stimulation lead 14 for applying the stimulation signal to the target brain tissue. In operation, both of these primary components are implanted in the person's body. The stimulation source 12 may be coupled to a connecting portion 16 of the electrical stimulation lead 14. The stimulation source 12 controls the electrical signals transmitted to at least one electrode 18 located on a stimulating portion 20 of the electrical stimulation lead 14, located adjacent the target brain tissue. The stimulation source 12 may control the electrical signals according to suitable signal parameters (e.g., duration, intensity, frequency, etc., of pain). A physician, the patient, or another user of the force-regulatable device 10 may directly or indirectly input signal parameters for controlling the nature of the electrical stimulation provided. Other examples of stimulation devices include a microstimulator (i.e., Bion™, manufactured by Advanced Bionics Corporation) in which the device contains a signal generating portion and at least one electrode in the same unit or single unit, as defined in U.S. Pat. Nos. 6,051,017; 6,735,475 and 6,735,474, each of which is incorporated by reference herein in its entirety.

Applying the electrical stimulation to the target brain tissue comprises applying electrical stimulation from about 1 Volt (V) to about 25 V and at a frequency from about 10 Hertz (Hz) to about 200 Hz. Alternatively, electrical stimulation may be applied from about 1 V to about 5 V and at a frequency from about 110 Hz to about 135 Hz.

Yet another embodiment of the method of the present invention comprises a collapsible/expandable electrode that is mechanically adjustable to apply the optimum amount of mechanical force necessary to treat chronic nociceptive pain. The collapsible/expandable electrode may be controlled manually (e.g., by a patient or physician) or automatically to alter the nociceptive pain signals in or about the brain area that processes nociceptive pain signals. Automatic control may further be associated with a detectable signal, such as nociceptive pain.

Yet another embodiment of the method of present invention comprises implanting the epidural or subdural force-regulatable device in chemical communication with a brain area and applying a chemical (e.g., a neurotransmitter or a pain reliever) from a chemical source to the brain area. The brain area may be, for example, the motor cortex.

In another aspect, the invention comprises a system for treating chronic nociceptive pain by implanting at least one force-regulatable device about and in mechanical, electrical, or chemical communication with a brain area that processes nociceptive pain signals. The force-regulatable device may be in electrical communication with at least an electrical power source for applying electrical energy to the brain area. In addition, at least the mechanical or electrical communication of the force-regulatable device acts on the brain area (e.g., the motor cortex) to alleviate chronic nociceptive pain. In one embodiment, the system of the invention further comprises identifying a brain area involved in processing nociceptive pain signals prior to implanting a force-regulatable device.

Referring back to FIG. 1, a stimulation source 12 that includes an implantable electrical power source in the form of an internal pulse generator (IPG) is illustrated. A person having ordinary skill in the art is aware that any commercially available implantable pulse generator may be used in the present invention, as well as a modified version of any commercially available pulse generator. Thus, a person having ordinary skill in the art would be able to select or modify an IPG to achieve the desired results. IPGs may include, for example, implantable battery-powered power sources manufactured by Medtronic, Inc., such as the Itrel 3, Synergy®, SynergyPlus®, SynergyCompact+™, or the rechargeable Restore® neurostimulator power sources.

Alternatively, an extension (not shown) may be used to conduct electricity from the power source 12 to the lead 14. The extension may be bifurcated and of various lengths.

Leads 14 suitable for use with the power source 12 include, for example, surgically implantable leads such as the Resume II® or Resume TL® leads manufactured by Medtronic Inc. The leads are typically quadripolar with multiple electrodes 18. Other suitable leads will be known to a person of ordinary skill in the art.

FIG. 2 depicts an example of a force-regulatable device 10 having an IPG. FIG. 2 shows the stimulation source 12 including an implantable wireless receiver 19. An example of a wireless receiver 19 may be one manufactured by Medtronic, Inc., such as the Mattrix® receiver. The wireless receiver 19 is capable of receiving wireless signals 24 from a wireless transmitter 22 located external to the person's body (not shown). A doctor, the patient, or another user of the force-regulatable device 10 may use a controller 26 located external to the person's body to provide control signals 24 for operation of the stimulation source 12.

The controller 26 provides control data to the wireless transmitter 22. In turn, the wireless transmitter 22 transmits the control signals 24 to the wireless receiver 19 of the stimulation source 12. The stimulation source 12 then uses the control signals 24 to vary the signal parameters of electrical signals transmitted through the electrical stimulation lead 14 to the electrode 18 and accordingly the stimulation site (e.g., the motor cortex).

Implantation of Electrical Stimulation Devices

While not being bound by the description of a particular procedure, patients who are to have an electrical stimulation lead or electrode implanted onto the brain, generally, first undergo a mapping or scanning procedure to obtain details regarding a given patient's neuroanatomy. Those of ordinary skill in the art know these methods. Upon completion of the mapping procedure the map is correlated to a three dimensional stereotactic frame of reference in the real surgical field. The map may then be recalled during surgery (e.g., using the Stealth navigational system "trained" by MRI scans) to pinpoint the desired brain region of interest (e.g., the motor cortex).

In order to align the two coordinate frames, both the instruments and the patient should be situated in correspondence to the virtual map. In one embodiment, this is accomplished by rigidly mounting the head frame to the surgical table. Subsequently, a series of reference points are established to relative aspects of the frame and the patient's skull, so that either a person or a computer software system can adjust and calculate the correlation between the real world of the patient's head and the virtual space model of the patient's MRI scans. See FIG. 3. The surgeon is able to target any region within the stereotactic space of the brain with precision (i.e., within 1 mm). Initial anatomical target localization is achieved either directly using the MRI images, or indirectly using interactive anatomical atlas programs that map the atlas image onto the stereotactic image of the brain.

Figure 4:
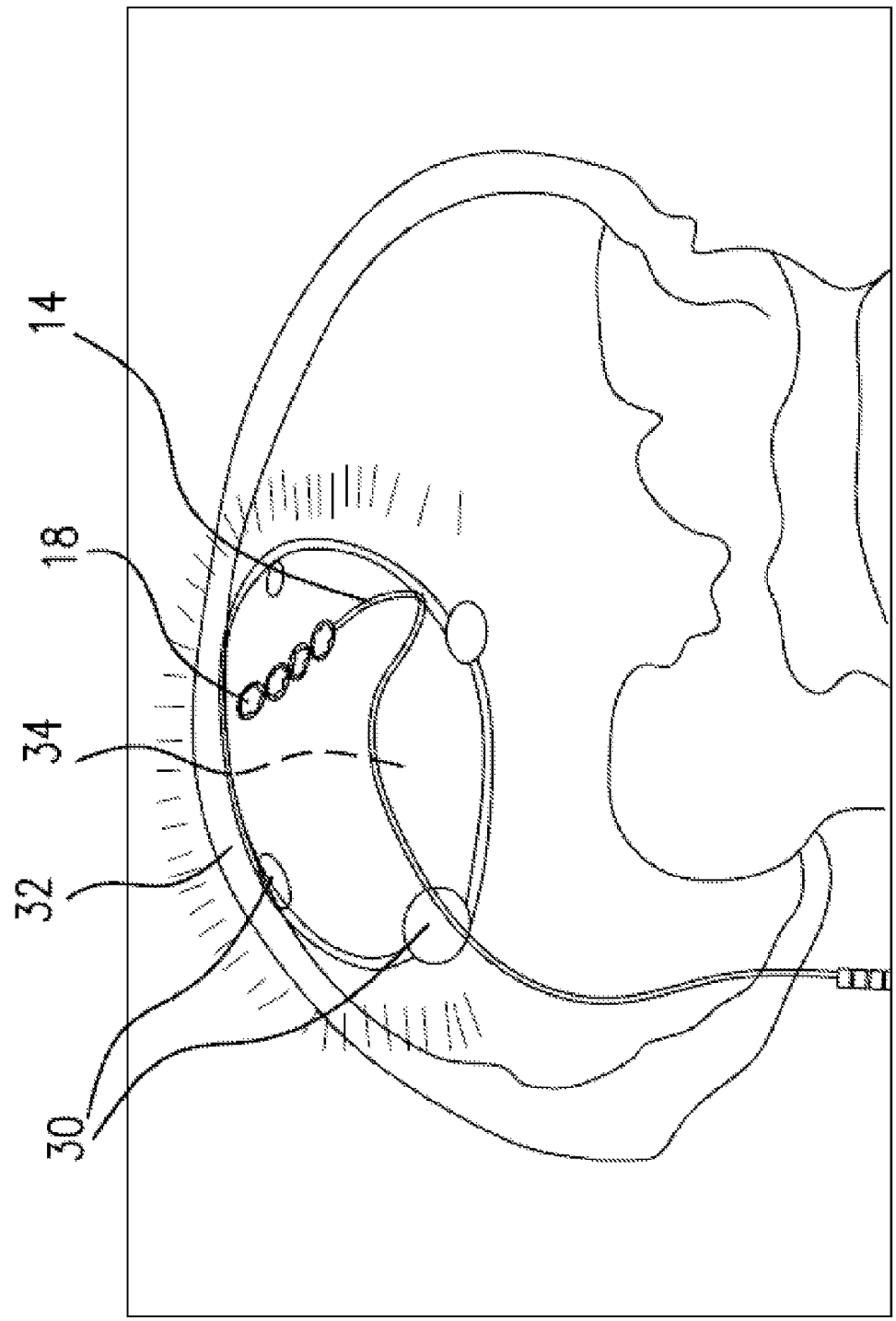
FIG. 4 illustrates an X-ray showing a human skull and brain with electrodes placed along the motor cortex.

Referring to FIG. 4, the electrical stimulation lead 14 can be positioned on the brain 34 based upon the coordinates derived from the mapping or scanning procedure. An insertion cannula (not shown) may be used to insert the electrical stimulation lead 14 through a burr hole 30 drilled through a skull 32. Alternatively, a hollow needle may provide the cannula. The cannula (not shown) and electrical stimulation lead 14 may be inserted together or lead 14 may be inserted through the cannula after the cannula has been inserted.

Once the electrical stimulation lead 14 and electrode(s) 18 are positioned on a brain 34, the lead is uncoupled from any stereotactic equipment present, and the cannula and stereotactic equipment are removed. Where stereotactic equipment is used, the cannula may be removed before, during, or after removal of the stereotactic equipment. Connecting portion 16 (see FIG. 1 and FIG. 2) of electrical stimulation lead 14 is laid substantially flat along the skull 32. Where appropriate, any burr hole cover (not shown) seated in a burr hole 30 may be used to secure the electrical stimulation lead 14 in position and possibly to help prevent leakage from the burr hole and entry of contaminants into the burr hole. Example burr hole covers that may be appropriate in certain embodiments are illustrated and described in U.S. Patent Application Publication No. 20050143799 which is incorporated by reference herein in its entirety.

Once electrical stimulation lead 14 has been inserted and secured, connecting portion 16 of the lead 14 and electrode(s) 18 extends from the lead insertion site to the implant site, in this case the motor cortex of the brain 34. In one embodiment, the stimulation source 12 may also be implanted about the implant site for the lead 14 and electrode(s) 18 (e.g., subdurally). The implant site is typically a subcutaneous pocket formed to receive and house the stimulation source 12. In another embodiment, the implant site is usually positioned a distance away from the insertion site, such as near the chest, below the clavicle, near the buttocks, or another place in the torso area. Once all of the appropriate components of the stimulation system are implanted, these components may be subject to mechanical forces and movement in response to movement of the person's body. A doctor, the patient, or another user of stimulation source 12 may directly or indirectly input signal parameters for controlling the nature of the electrical stimulation provided.

In other embodiments, a drug delivery system independent of or in combination with electrical stimulation of the brain may be utilized. Drug delivery may be used independent of or in combination with a lead or electrode to provide electrical stimulation or chemical stimulation. A drug delivery catheter (not shown) may be implanted such that the proximal end of the catheter is coupled to a pump and a discharge portion for infusing a dosage of a pharmaceutical or drug. Implantation of the catheter may be achieved by combining data from a number of sources, including computed tomography scan (i.e., CT, or "CAT" scan), MRI or conventional or magnetic resonance angiography into the stereotactic targeting model. Thus, without being bound to a specific procedure, implantation of the catheter can be achieved using similar techniques as discussed above for implantation of electrical leads and electrodes. The distal portion of the catheter can have multiple orifices to maximize delivery of the pharmaceutical while minimizing mechanical occlusion. The proximal portion of the catheter can be connected directly to a pump or via a metal, plastic, or other hollow connector, to an extending catheter.

Any type of infusion pump known to a person of ordinary skill in the art may be used in the present invention. For example, "active pumping" devices or so-called peristaltic pumps are described in U.S. Pat. Nos. 4,692,147, 5,840,069, and 6,036,459, which are incorporated herein by reference in their entirety. Peristaltic pumps are used to provide a metered amount of a drug in response to an electronic pulse generated by control circuitry associated within the device. An example of a commercially available peristaltic pump is SynchroMed® implantable pump from Medtronic, Inc., Minneapolis, Minn.

Other pumps that may be used in the present invention include accumulator-type pumps, for example certain external infusion pumps from Minimed, Inc., Northridge, Calif. and Infusaid® implantable pump from Strato/Infusaid, Inc., Norwood, Mass. Passive pumping mechanisms can be used to release an agent in a constant flow or intermittently or in a bolus release. Passive type pumps include, for example, but are not limited to, gas-driven pumps described in U.S. Pat. Nos. 3,731,681 and 3,951,147; and drive-spring diaphragm pumps described in U.S. Pat. Nos. 4,772,263, 6,666,845, 6,620,151, each of which is incorporated by reference in its entirety. Pumps of this type are commercially available, for example, Model 3000® from Arrow International, Reading, Pa. and IsoMed® from Medtronic, Inc., Minneapolis, Minn.; AccuRx® pump from Advanced Neuromodulation Systems, Inc., Plano, Tex.

In another aspect of the system of the invention, the force-regulatable device may apply a regulatable mechanical force to the motor cortex with or without electrical or chemical stimulation to treat chronic nociceptive pain. For example, a force-regulatable device may include a collapsible/expandable electrode or a bulb-type device capable of changing shape in order to apply mechanical pressure to a brain area. (See, e.g., the force-regulatable electrode described in U.S. Patent Application No. 2005/0203602 to Wallace et al., which is incorporated by reference in its entirety; see also, for example, the force-regulatable system or device 10 in FIG. 1 or FIG. 2). The devices described herein may be used to provide such a force. Mechanical force application to the motor cortex may lead to a striking and long-lasting (several weeks to months) alleviation of chronic nociceptive pain. Supplementing or replacing the mechanical force stimulation with electrical (such as, for example electrical stimulation lead 14 and electrode 18 in FIG. 2 or FIG. 4) or chemical stimulation may provide long-term alleviation of chronic nociceptive pain from, for example, arthritis. The mechanical force may be applied on command or intermittently in a titrated and tightly controlled manner, such as through mechanical expansion or deformation of the device. In addition, chemical stimulation may be used to induce a localized, beneficial inflammatory response. A beneficial inflammatory response may include alleviation of nociceptive pain via a change in brain function or a disruption in the pathological process of nociceptive pain. By way of example, there may be an inflammatory post-operative response following the placement of an object (e.g., an electrode) onto the brain See, e.g., 34 in FIG. 3 or FIG. 4). This may change the brain activity in the area in which the object was placed, which could beneficially disrupt or change the pathological activity that is manifested as nociceptive pain.

The mechanical communication between the electrode and the motor cortex may include a regulatable inflammatory response. For example, the mechanical communication may generate new electrical activity that interferes or disrupts the neural activity underlying, in this case, chronic nociceptive pain. This embodiment may be combined with other embodiments discussed herein. Chemical or mechanical stimulation—including a pressure effect—via a chemical or a controlled and regulated biological foreign body or inflammatory response to an implanted force-regulatable device may be used to produce a therapeutic benefit.

The systems of the present invention, whether comprising devices for providing a stimulus, comprising electrical stimulation, chemical or mechanical modulation, may provide a stimulus to the brain area of the patient in an on-going continuous manner, or may be controlled or regulated by the patient or by a care-giver. The system may comprise a device for providing a stimulus, whether electrical stimulation, chemical or mechanical modulation, and the device may be in a closed loop system wherein the delivery of the stimulus, which may be electrical stimulation, chemical or mechanical modulation, is controlled. The control of the delivery of the stimulus and the determination of initiation, continuation, adjustment of amount, level, rate, location, or cessation of the stimulus may be provided in response to a predetermined signal. Such a predetermined signal may be a physiological change in the patient, including but not limited to, an electrical signal from for example, an EEG, field potential, evoked potential, or a neuronal firing pattern; a chemical signal, for example, a change in concentration of lactate, potassium ions, or pH in bodily fluid or structure; or a physical signal such as tissue pressure, temperature, change in optical properties of the tissue, change in motor function such as cessation of tremor, or a change resulting from lowered pain perception. Such a predetermined signal may be a particular reading or setting from a monitoring device that measures one or more physiological parameters of the patient. The predetermined signals are detected, processed and used to control the delivery of the stimulus. Signal detection and the resulting signal processing steps and devices to accomplish such steps may be located locally or remotely from the site of therapeutic delivery of the stimulus. The system may comprise such signal detection devices, processing devices, monitoring devices, and connections therebetween.

As an example, the system of the present invention may have a closed loop arrangement where the force is applied based on an input signal (e.g., tremor, EEG signal, etc.). This signal is then transmitted to a processor (not shown) and a signal output generator (not shown) to the mechanical device. The mechanical force may include on-off variable duration cycles and may further be coupled to a device (not shown) to deliver electrical stimulation or chemical stimulation. This approach utilizing mechanical force stimulation, electrical stimulation, or chemical stimulation in series may prolong battery life and may possibly work synergistically to alleviate chronic nociceptive pain compared to any one of the stimulations used alone.

In another aspect, the system of the present invention may include functional imaging to identify and target areas of abnormal brain activity relative to nociceptive pain, chronic nociceptive pain, and non-nociceptive pain such as deafferentation pain, neuropathic pain, and central pain. In this manner, altering the nociceptive pain signals in the identified brain area could be customized or individualized for a given patient. In one embodiment, the system for using functional imaging to identify and target areas of abnormal brain activity could compare baseline brain activity in pain patients with that of control subjects without pain. Furthermore, the pain patients could be given a pain stimulus—such as heat applied to the skin—to more precisely map the brain area activated by the painful stimulus and thus target this area for disruption or alteration of nociceptive pain signals, thus alleviating chronic nociceptive pain. The heat applied to the patient's skin may range, for example, from about 44° C. to about 50° C. Furthermore, the painful heat stimulus may be applied in increasing increments of one degree C. to precisely map and target the brain area that is stimulated by the painful stimulus. Brain areas in which this could be accomplished include, but are not limited to, the cingulate lobe, the insula, the primary sensory cortex, the secondary sensory cortex, the medial thalamus, the lateral thalamus, the reticular formation, the neural pathways coursing from the brainstem to the thalamus, the neural pathways coursing from the brainstem to the cortex, and the motor cortex (i.e., the motor cortex, the premotor cortex, the primary motor cortex, or the supplementary motor cortex areas). The imaging could be accomplished using fMRI, magnetoencephalography, evoked potentials, or PET. Other appropriate imaging techniques are known to those of ordinary skill in the art. In another embodiment, the system for using functional imaging to identify and target areas of abnormal brain activity may utilize imaging machines designed for intraoperative imaging such that pain patients may act as their own controls to identify and target areas of abnormal brain activity relative to chronic nociceptive pain.

In general, the methods and systems of the present invention comprise methods and systems for treating or alleviating nociceptive pain. A method for treating nociceptive pain, comprises, contacting a brain area that processes nociceptive pain signals using a force-regulatable device; applying mechanical, electrical, or chemical stimulation to the brain area; and alleviating nociceptive pain by altering the nociceptive pain signals in the brain area. The method further comprises identifying the brain area that processes nociceptive pain signals prior to contacting the brain area using a force-regulatable device. Such identifying may visualizing the brain using magnetic resonance imaging, functional magnetic resonance imaging, positron emission tomography, magnetoencephalography, evoked potentials, or direct cortical stimulation. Areas of the brain include, but are not limited to, the cortex, the motor cortex, the primary motor cortex area, the premotor cortex area, or the supplementary motor cortex area, the nucleus accumbens, the anterior limb of the internal capsule, the cingulated gyms including Brodmann area 25, the subcallosal area, the insula, orbital frontal and medial frontal lobes; or the dorsolateral frontal lobe. Contacting one or more brain areas may comprise surgically implanting the force-regulatable device. Applying mechanical stimulation may comprise manual or automatic operation of a collapsible/expandable force-regulatable device. Applying electrical stimulation may comprise supplying at least one force-regulatable device with electrical power.

The force-regulatable device may be in communication with an electrical power source to provide electrical stimulation to the motor cortex area.

Chemical stimulation may comprise ionic solutions, containing potassium ions ($K^+$) or sodium ions ($Na^+$), neurotransmitters, norepinephrine, glycine, aspartic acid, aspartate, glutamic acid, glutamate, gamma-amino butyric acid (GABA), acetylcholine, dopamine, or serotonin, medications that increase the level of a neurotransmitter flouxetine, Prozac®), trazodone, chemicals or compounds that act to inhibit axonal or neuronal activity, local anaesthetics, lidocaine, marcaine, a drug that acts to block pain, a pain reliever, morphine or its derivatives, or opioid peptides such as endorphins, enkephalins, or dynorphins.

Methods for treating chronic nociceptive pain, comprise implanting at least one force-regulatable device in mechanical, electrical, or chemical communication with at least one brain area that processes nociceptive pain signals; and applying mechanical, electrical, or chemical stimulation to the at least one brain area; wherein the force-regulatable device is in communication with an electrical power source, a mechanical power source, or a chemical source. The method may further comprise identifying a brain area that processes nociceptive pain signals prior to implanting the at least one force-regulatable device. Identifying may be by methods known to those skilled in the art. The at least one brain area may be the ones listed herein or may be other brain areas associated with nociceptive pain. Implanting at least one force-regulatable device may comprise securing a collapsible/expandable electrode about the dura such that the collapsible/expandable electrode exerts a mechanical force on the brain area. The collapsible and/or expandable electrode may comprise adjustable settings for applying mechanical force. The collapsible/expandable electrode may comprise manual control means or automatic control means; wherein the automatic control means may be associated with a detectable signal. The detectable signal may comprise the sensation of nociceptive pain. Applying electrical stimulation to the brain area may comprise applying electrical stimulation from about 1 V to about 25 V and from about 10 Hz to about 200 Hz frequency. Applying electrical stimulation to the brain area may comprise applying electrical stimulation at from about 1 V to about 5 V and from about 110 Hz to about 135 Hz frequency.

Chemical stimulation of the at least one brain area may comprise applying a neurotransmitter or a pain reliever from the chemical source to the brain area, or applying ionic solutions comprising potassium ions ($K^+$) or sodium ions ($Na^+$). Methods also comprise applying two or more of mechanical, electrical or chemical stimulation to the at least one brain area.

The current invention also comprises systems for treating or alleviating chronic nociceptive pain, comprising, a force-regulatable device in mechanical, electrical, or chemical communication with a brain area that processes nociceptive pain signals; wherein the force-regulatable device is implanted about a patient's body to alter the nociceptive pain signals in the brain area. The system may further comprise a an imaging device for identifying a brain area involved in processing nociceptive pain signals prior to implanting the force-regulatable device. Such imaging devices include, but are not limited to devices for magnetic resonance imaging, functional magnetic resonance imaging, positron emission tomography, electroencephalogram, magnetoencephalography, evoked potentials; or direct cortical mapping. Identification of particular brain areas may be accomplished by any means known to those skilled in the art, including, but not limited to, stimulating a patient with a painful stimulus in order to identify the brain area. Use of the system described herein of a force-regulatable device in mechanical, electrical, or chemical communication with the at least one brain area alleviates bilateral nociceptive pain. The force-regulatable device in mechanical communication with the brain area may comprise a collapsible/expandable electrode, which may be connected to or derived from a manually activated electrical power source. The electrical communication may be derived from a programmable power source programmed to initiate electrical communication with the brain area upon pain sensation. Chemical communication may comprise a neurotransmitter or a pain reliever to alter the nociceptive pain signals. Mechanical or chemical communication may comprise a localized regulatable inflammatory response. Electrical communication may comprise applying electrical stimulation from about 1 V to about 25 V and from about 10 Hz to about 200 Hz frequency to the primary motor cortex, or applying electrical stimulation from about 1 V to about 5 V and from about 110 Hz to about 135 Hz frequency to the primary motor cortex.

It must be noted that, as used in this specification and the appended claims, the singular forms "a", "an", and "the" include plural referents unless the context clearly dictates otherwise.

All patents, patent applications and references included herein are specifically incorporated by reference in their entireties.

It should be understood, of course, that the foregoing relates only to exemplary embodiments of the present invention and that numerous modifications or alterations may be made therein without departing from the spirit and the scope of the invention as set forth in this disclosure.

Although the exemplary embodiments of the present invention are provided herein, the present invention is not limited to these embodiments. There are numerous modifications or alterations that may suggest themselves to those skilled in the art.

The present invention is further illustrated by way of the examples contained herein, which are provided for clarity of understanding. The exemplary embodiments should not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1

Example 1 is representative of the procedure to implant a lead and electrode in accordance with the system and method for treating pain of the current invention. The patient was a 67-year-old male with medically refractory essential tremor. The patient opted to undergo placement of a motor cortex stimulator as part of an ongoing clinical trial.

After informed consent was obtained, the patient was brought to the operating room. He was positioned on his right side with a beanbag and axillary roll. Perioperative antibiotics were administered. With local anesthesia and conscious sedation, the patient was placed in a Mayfield head holder. The previously placed fiducials were registered using a Stealth workstation. The Stealth workstation was used to plan out the incision and craniotomy. The fiducials were removed. The hair was removed with clippers and a wet shave. The patient was prepped and draped using a standard sterile technique. After infiltration with local anesthetic, a horseshoe shaped incision was made over the left parietal region. Raney clips were used for hemostasis.

Monopolar cautery was used to incise the temporalis fascia and muscle. The temporalis muscle and skin flap were reflected inferiorly while leaving a cuff of temporalis fascia for closure. A craniotomy was performed. A high speed drill was used to create burr holes in the adjacent skull through which dural tack ups were placed. The dura was opened in a cruciate fashion. The Stealth was used to localize the motor cortex. Intraoperative mapping was performed. The patient's sensory cortex was mapped by inducing sensory perceptions. The motor cortex was mapped by inducing motor contractions in response to electrical stimulation. At 7 milliamps, 100 microseconds and 50 hertz, the patient did not report any paresthesias or motor contractions. When this was increased to 11 milliamps, the sensory cortex and motor cortex were mapped. With stimulation of the motor strip, the patient's tremor was reset. A Resume® electrode was placed over the motor cortex and secured in place to the overlying dura (i.e., subdural placement) using 4-0 Nurolon's. The electrode was connected to an extension and an IPG with the patient under general anaesthesia. Irrigation was crystal clear. The dura was closed using 4-0 Nurolon's.

The bone flap was replaced using 1-0 Vicryl's. The distal wire from the resume electrode was brought out through the more anterior inferior burr hole. Gaps from the remaining bur holes were filled with bone dust. The temporalis fascia was closed using 3-0 Vicryl's. A percutaneous extension was brought out through a separate stab incision behind the left ear. The resume electrode was connected to the percutaneous extension. The scalp was closed in two layers using 3-0 Vicryl's and staples. A 2-0 Nylon was used to secure the percutaneous extension with a purse string. Dry sterile dressings were placed over the patient's scalp.

Example 2

During an experimental trial of cortical stimulation in four patients with essential tremor, two patients with nociceptive pain in the knee joints from osteoarthritis reported a reduction in pain. The other two patients did not have preexisting pain.

The reduction in pain began immediately after surgery and has been bilateral. It occurred with the introduction of an electrode array (Medtronic Resume® electrode) measuring approximately 8 cm long by 1 cm wide and 2 mm thick over the primary motor cortex in the subdural space. The pain reduction was long lasting from six weeks to several months in these patients. Introducing this electrode also had a striking benefit in arm tremor, which is also bilateral. The magnitude in the reduction of pain has been from "7" to "2" out of a maximum of "10" on a pain scale of 0 to 10.

In one of these patients suffering from severe osteoarthritis and essential tremor, a motor cortex stimulator (i.e., electrode) was placed in the subdural space according to Example 1. The osteoarthritis knee pain was bilaterally reduced from an "8" to a "3" on a pain scale of 0 to 10 after the insertion. Approximately six weeks after the insertion of the motor cortex electrode, however, the severity of the pain returned to its pre-operative baseline.

To address the issue of recurrent knee pain, electrical stimulation was applied via the electrode at between about 1 to 25 Volts (V), a pulse width of between about 60 microseconds (μsec) and 120 μsec, and a frequency of between about 30 hertz (Hz) and 200 Hz. The electrical stimulation reduced the bilateral knee pain to zero. This was repeatable and reproducible. When the electrical stimulation was turned off, the pain recurred within one hour. The pain was relieved when the electrical stimulation was reapplied.

From the foregoing, it will be appreciated that specific embodiments of the invention have been described herein for purposes of illustration. Various modifications may be made without deviating from the spirit and scope of the invention, which is set forth in the following claims.

What is claimed is:

1. A method for treating nociceptive pain, comprising:
  contacting at least one region of the brain using a force-regulatable device;
  applying a mechanical stimulus to the at least one region of the brain to alter nociceptive pain signals; and
  alleviating nociceptive pain by altering the nociceptive pain signals in the at least one region of the brain, wherein the at least one region of the brain comprises the nucleus accumbens, the anterior limb of the internal capsule, the subcallosal cingulate area, the orbital frontal lobes, medial frontal lobes or dorsolateral frontal lobes.

2. The method of claim 1, further comprising identifying the brain region prior to contacting the at least one region of the brain using a force-regulatable device.

3. The method of claim 1, wherein contacting the at least one region of the brain comprises surgically implanting the force-regulatable device.

4. The method of claim 1, further comprising providing an electrical stimulus.

5. The method of claim 1, further comprising providing a chemical stimulus comprising ionic solutions comprising potassium ions (K+) or sodium ions (Na+), neurotransmitters comprising norepinephrine, glycine, aspartic acid, aspartate, glutamic acid, glutamate, gamma-amino butyric acid (GABA), acetylcholine, dopamine, or serotonin, medications that increase the level of a neurotransmitter, such as flouxetine and trazodone, chemicals or compounds that act to inhibit axonal or neuronal activity, local anesthetics, such as lidocaine and marcaine, or drugs that act to block or relieve pain, such as morphine or its derivatives, and opioid peptides, such as endorphins, enkephalins, and dynorphins.

6. The method of claim 1, wherein the at least one region of the brain is the medial frontal lobes.

7. The method of claim 1, wherein the at least one region of the brain is the subcallosal cingulated area.

8. A method for treating chronic nociceptive pain, comprising:
- implanting at least one force-regulatable device in mechanical communication with at least one region of the brain; and
- applying mechanical stimulation to the at least one region of the brain to alter nociceptive pain signals; wherein the force-regulatable device is in communication with a mechanical power source, and wherein the at least one region of the brain comprises the nucleus accumbens, the anterior limb of the internal capsule, the subcallosal cingulate area, the orbital frontal lobes, the medial frontal lobes or the dorsolateral frontal lobes.

9. The method of claim 8, comprising identifying the at least one region of the brain prior to implanting the at least one force-regulatable device.

10. The method of claim 8, wherein implanting the at least one force-regulatable device comprises securing the force-regulatable device about the dura such that the force-regulatable device exerts a mechanical force on the at least one region of the brain.

11. The method of claim 8, further comprising applying electrical stimulation to the at least one region of the brain.

12. The method of claim 11, wherein the stimulation comprises applying electrical stimulation from about 1 V to about 25 V and from about 10 Hz to about 200 Hz frequency.

13. The method of claim 8, further comprising providing a chemical stimulus comprising ionic solutions comprising potassium ions (K+) or sodium ions (Na+), neurotransmitters comprising norepinephrine, glycine, aspartic acid, aspartate, glutamic acid, glutamate, gamma-amino butyric acid (GABA), acetylcholine, dopamine, or serotonin, medications that increase the level of a neurotransmitter, such as flouxetine and trazodone, chemicals or compounds that act to inhibit axonal or neuronal activity, local anesthetics, such as lidocaine and marcaine, or drugs that act to block or relieve pain, such as morphine or its derivatives, and opioid peptides, such as endorphins, enkephalins, and dynorphins.

14. The method of claim 8, wherein the at least one region of the brain is the medial frontal lobes.

15. The method of claim 8, wherein the at least one region of the brain is the subcallosal cingulated area.

* * * * *